United States Patent [19]

Mauldin et al.

[11] 4,433,679
[45] Feb. 28, 1984

[54] KNEE AND ELBOW BRACE

[76] Inventors: Donald M. Mauldin, 3631 Potomac, Dallas, Tex. 75235; Richard E. Jones, III, 5804 Prestonview, Apt. 1089, Dallas, Tex. 75240

[21] Appl. No.: 426,981

[22] Filed: Sep. 29, 1982

Related U.S. Application Data

[63] Continuation-in-part of Ser. No. 260,075, May 4, 1981, Pat. No. 4,370,977.

[51] Int. Cl.³ .............................................. A61F 3/00
[52] U.S. Cl. .................................................. 128/80 F
[58] Field of Search ............... 128/80 R, 80 C, 80 F, 128/80 E, 83, 87 R, 88

[56] References Cited

U.S. PATENT DOCUMENTS

| | | | |
|---|---|---|---|
| 1,072,369 | 9/1913 | Spahn | 128/80 F |
| 1,939,097 | 12/1933 | Bauman | 128/80 F |
| 2,267,848 | 12/1941 | Taylor | 128/80 E |
| 2,410,560 | 11/1946 | Witte | 128/80 F X |
| 2,536,454 | 1/1951 | McIntyre | 128/80 F |
| 2,567,195 | 9/1951 | Ellery | 128/80 E |
| 2,632,440 | 3/1953 | Hauser et al. | 128/80 F |
| 2,883,982 | 4/1959 | Rainey | 128/80 F |
| 3,528,412 | 9/1970 | McDavid | 128/80 F |
| 3,732,861 | 5/1973 | Lehneis | 128/80 F X |
| 3,779,654 | 12/1973 | Horne | 128/80 C X |
| 3,853,123 | 12/1974 | Moore | 128/80 C |
| 3,935,858 | 2/1976 | Harroff | 128/80 C |
| 4,088,130 | 5/1978 | Applegate | 128/80 F |

FOREIGN PATENT DOCUMENTS 813501 10/1955 United Kingdom .

*Primary Examiner*—John D. Yasko

[57] ABSTRACT

A knee brace (400) includes a first hinge portion (408) having a face (426) comprising a plurality of circumferentially equally spaced teeth (428). An adjusting disc (440) has a first circular face (442) comprising teeth (448) which mesh with the teeth (428) of the first hinge portion (408) to lock the component parts of the knee brace (400) in any desired angular relationship. A second hinge portion (418) has a face (436) comprising a plurality of slots (438a, 438b, 438c and 438d). The adjusting disc (440) has a second circular face (444) comprising a tooth (450) which is selectively engageable with one of the slots (438a, 438b, 438c or 438d) of the second hinge portion (418) to regulate angular movement between the component parts of the knee brace (400). A torsion spring (462) has projections (468, 470) which are selectively positionable in apertures (422, 432) of the first and second hinge portions (408, 418) to apply a predetermined torque to the component parts of the knee brace (400).

10 Claims, 18 Drawing Figures

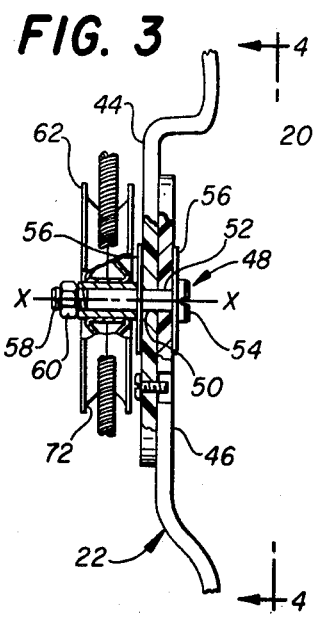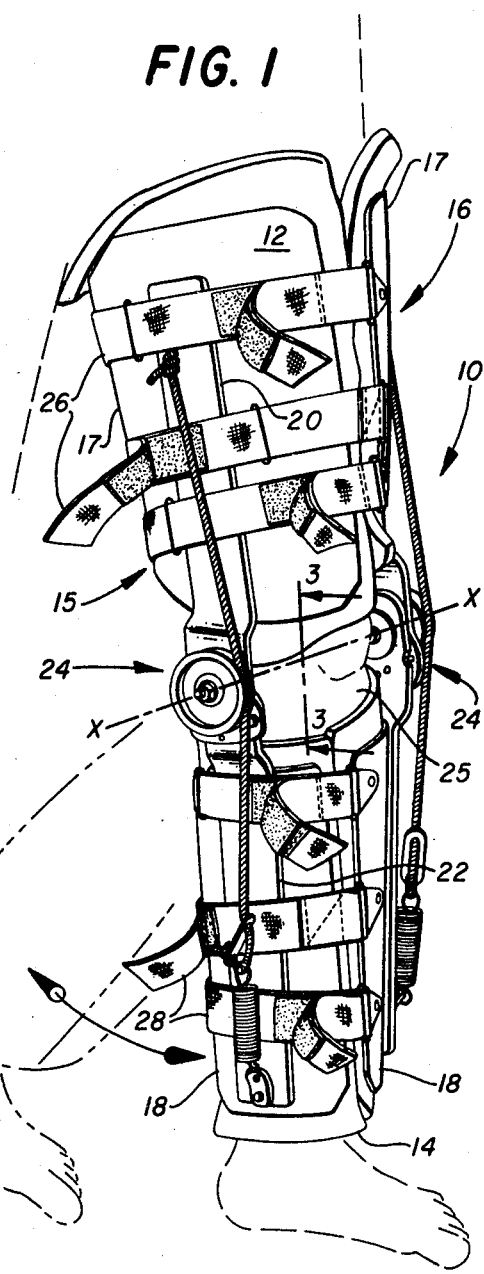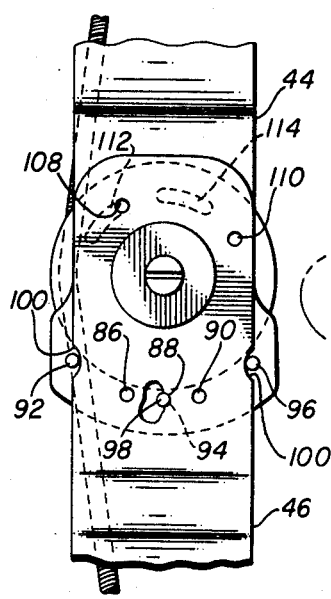

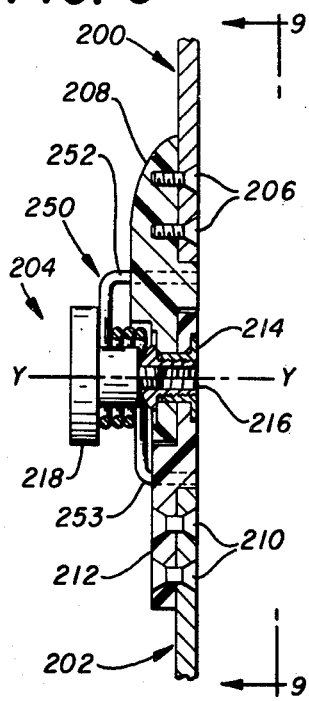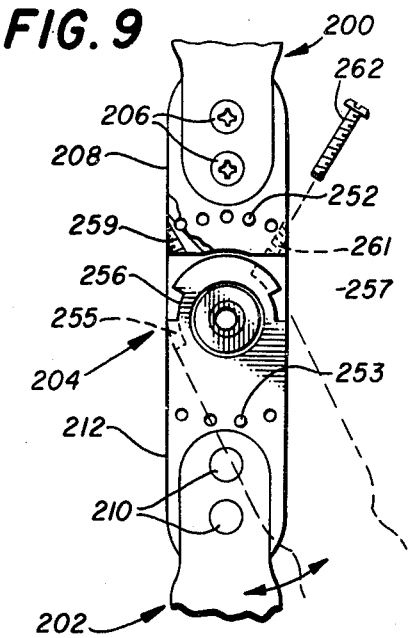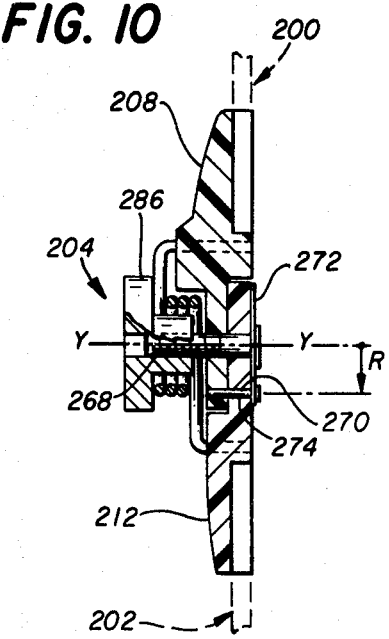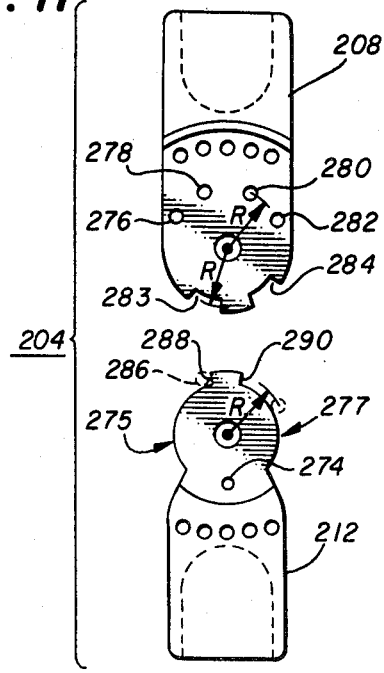

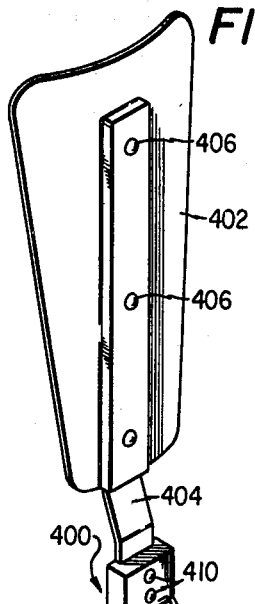
FIG. 16
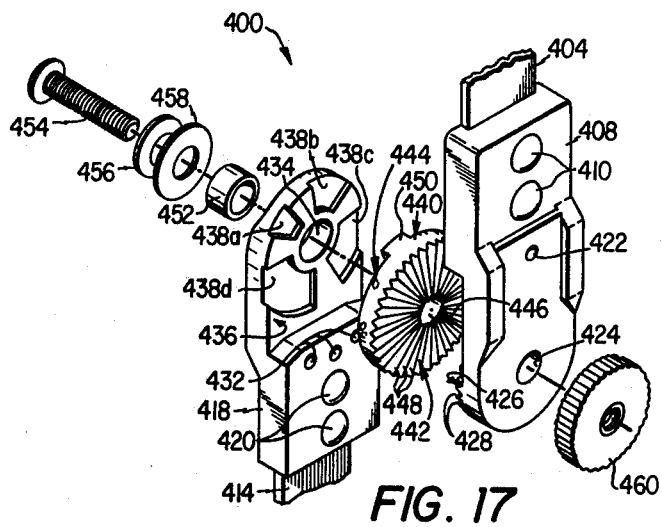
FIG. 17
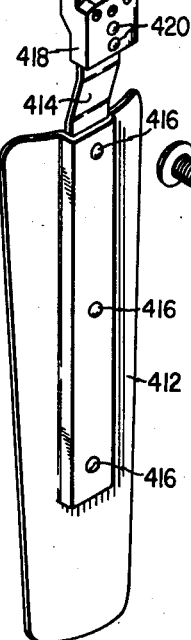
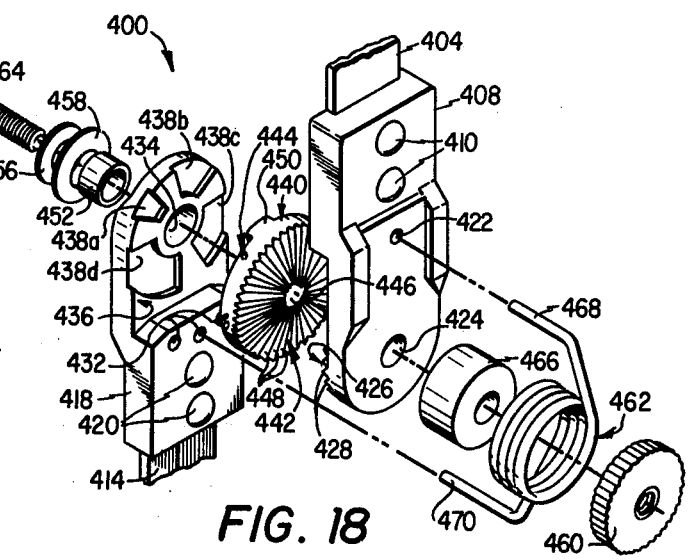
FIG. 18

KNEE AND ELBOW BRACE

CROSS REFERENCE TO RELATED APPLICATION

This application is a continuation-in-part of copending application Ser. No. 260,075 filed May 4, 1981, now U.S. Pat. No. 4,370,977.

TECHNICAL FIELD

This invention relates to patient care, and in particular to the stabilization and rehabilitation of a joint.

BACKGROUND ART

Braces for immobilizing joints in the human body are known. With particular reference to the lower extremity, devices are known which range from a full double upright conventional metal brace for permanent use in a neuromuscularly disabled individual to a knee immobilizer which incorporates metal stays with a soft foam and cloth outer body for nonrigid immobilization of knees after injuries and minor surgeries.

The present cloth and medal knee immobilizer is inadequate for other purposes and often fails to provide good immobilization of the knee joint. For example, an individual will initially have approximately 15° to 20° of knee flexion due to fluid on the knee joint after injury or surgery. Therefore, it is very painful to attempt to straighten the knee acutely to fit an immobilizer.

A number of braces have been developed to control knee stability which incorporate a knee hinge. One cast brace is made from a variety of casting materials in which various types of hinges have been designed, some of which limit the motion within a specific arc. At the present time, some orthopedists repairing the medial collateral ligament position a postoperative splint or full long leg cast to hold the knee between 30° and 60° of flexion. This position is maintained for three to four weeks. A plaster type cast brace is then applied which has hinges incorporated therein to allow motion between a 30° to 60° arc from full extension. This brace is worn for another four week period at which time this brace is removed and a knee immobilizer is applied to stabilize the joint. There is a tremendous cost involved with multiple cast changes. In addition, a knee immobilizer is ultimately required at the end of the cast immobilization period.

An additional problem encountered with known knee immobilizers relates to properly positioning the immobilizer on a patient. The common immobilizer having medial and lateral stays sewn permanently to the device should ideally be placed along the mid-lateral line medially and laterally on the leg. However, this occurs only if the circumference of the leg is appropriate for the size immobilizer. Without appropriate fit, the medial and lateral stays become anterior to the knee joint axis, if the device is too large. If the device is too small, the medial and lateral stays will be too far posterior to the knee. One immobilizer currently sold has movable medial and lateral stays, which somewhat improves the ability to properly position the immobilizer.

Another major problem with the known knee immobilizers are their inability to be positioned on a patient with a conical shaped thigh. This shape is the most common in individuals and therefore great difficulty arises in maintaining the immobilizer in the proper position. Finally, a knee immobilizer often does not provide rigid immobilization. A poor fit on a patient may permit flexure of the knee within a 30° arc.

SUMMARY OF THE INVENTION

In accordance with the present invention, a brace for supporting the regions adjacent a joint in the human body is provided. The brace includes first and second sections secured to the body on opposite sides of the joint. A hinge is interconnected between the first and second sections for pivotal motion about an axis substantially corresponding to the pivotal axis of the joint, the hinge permitting a pivotal motion between a preselected arc. A spring is provided for urging the first and second sections into a predetermined relationship to support the portions of the body about the joint in a desired relation.

In accordance with yet another aspect of the present invention, an elbow brace for supporting the regions adjacent the elbow is provided. The elbow brace includes first and second sections secured to the body on opposite sides of the elbow. A hinge interconnects the first and second sections for pivotal motion about an axis substantially corresponding to the pivotal axis of the elbow. Springs are interconnected between the first and second sections to urge the elbow into a desired position.

In accordance with yet another aspect of the present invention, a knee brace for support and rehabilitation of the knee joint and adjoining tissue is provided. The knee brace includes an upper leg section for attachment to the upper leg, the upper leg section being adjustable for use with a range of leg sizes. A lower leg section is provided for attachment to the lower leg, the lower leg section also being adjustable for use with a range of leg sizes. Hinges interconnect the upper and lower leg sections on each side of the knee joint, the hinges having a pivotal axis corresponding substantially to the pivotal axis of the knee joint. Locking structure is provided to lock the hinges in a set position to immobilize the knee joint. Limit structure is provided for limiting the pivotal motion of the hinges to permit the knee joint to move within a preselected arc. Springs interconnect the upper and lower leg sections for urging the hinges and knee joint to pivot to one preselected position.

Still another aspect of the invention relates to a hinge connection for a knee brace. An adjusting disc has one large tooth on one side and a plurality of small teeth on the opposite side. A first hinge portion has a plurality of small teeth which cooperate with the small teeth of the adjusting disc to establish a desired angular relationship between the component parts of the knee brace. A second hinge portion has a plurality of large tooth receiving notches each having a different circumferential dimension. Angular movement between the component parts of the knee brace is regulated by positioning the large tooth in a selected notch. A torsion spring may be employed to impose a predetermined pivotal movement on the component parts of the knee brace.

DESCRIPTION OF THE DRAWINGS

A more complete understanding of the invention may be had by reference to the following Detailed Description when taken in conjunction with the accompanying Drawings, wherein:

FIG. 1 is a perspective view of the first embodiment of the invention forming a knee brace;

FIG. 3 is a vertical cross-sectional view of a hinge member for use in the knee brace;

FIG. 4 is a side view of a hinge in the knee brace in the fully extended position;

FIG. 8 is a vertical cross-sectional view of the hinge in the first modification of the knee brace;

FIG. 9 is a side view of the hinge in the first modification of the knee brace taken along line 9—9 in the direction of the arrows in FIG. 8;

FIG. 10 is a vertical cross-sectional view of a hinge in the second modification of the knee brace;

FIG. 11 is a side view of the hinge in the second modification of the knee brace taken along line 11—11 in the direction of the arrows in FIG. 10;

FIG. 16 is a perspective view of a knee brace comprising a third embodiment of the invention;

FIG. 17 is an enlarged, exploded view of a portion of the knee brace of FIG. 16; and FIG. 18 is a view similar to FIG. 17 showing the use of a torsion spring in conjunction with the knee brace of FIG. 16.

DETAILED DESCRIPTION

Figure 2:
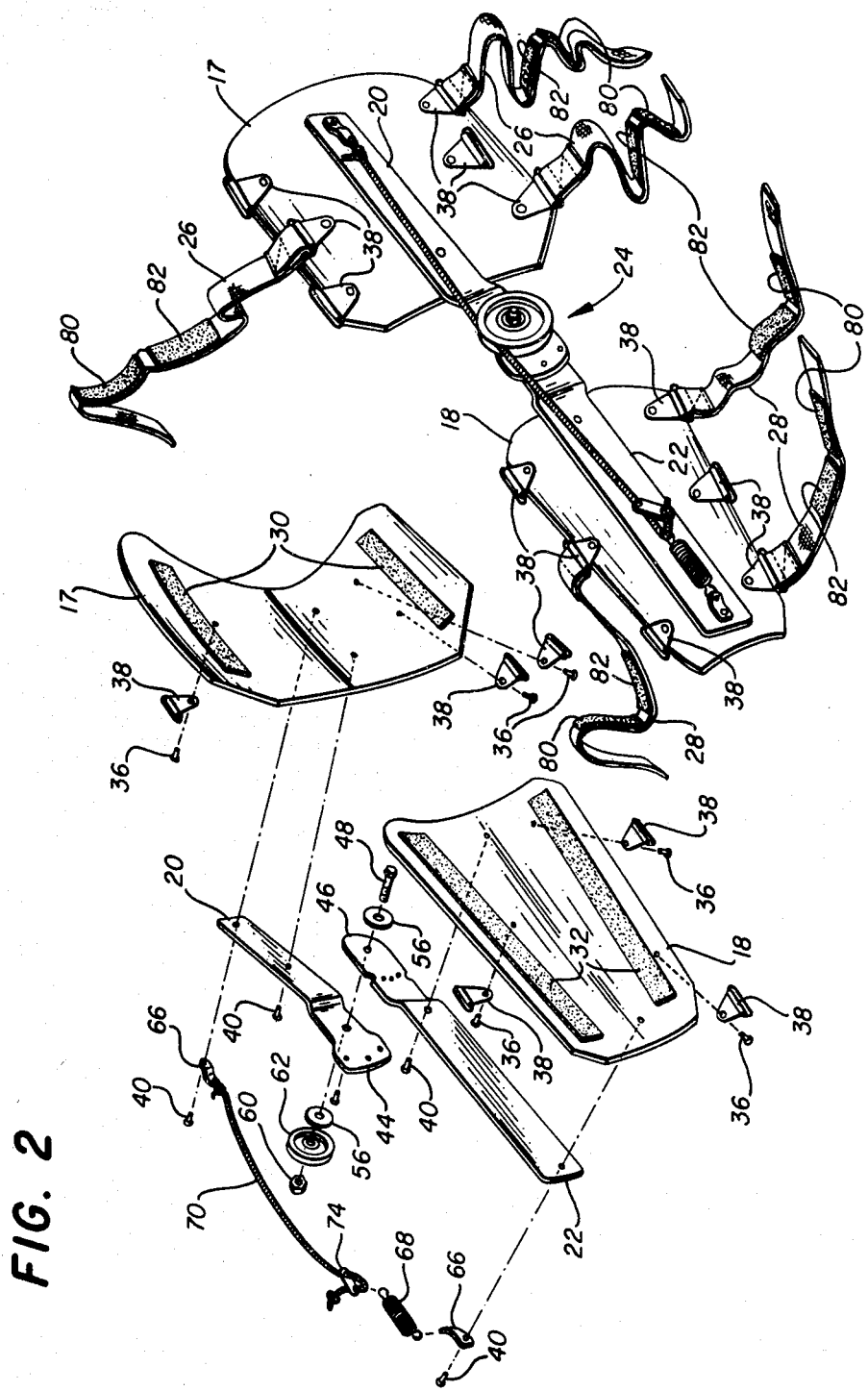
FIG. 2 is an exploded view of the knee brace.
Figure 5:
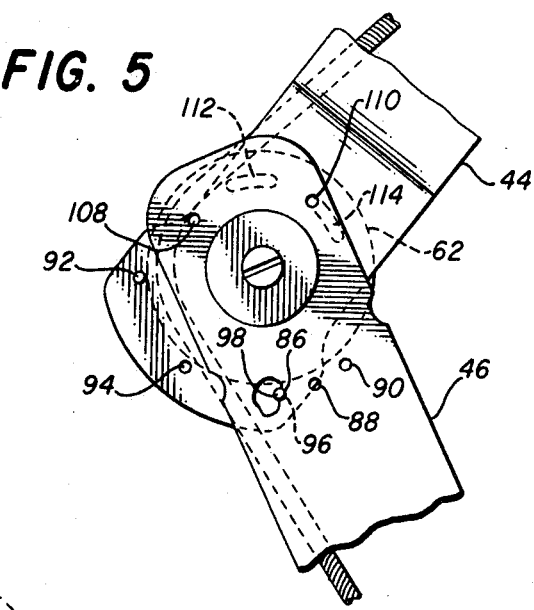
FIG. 5 illustrates the hinge of the knee brace in flexion.
Figure 6:
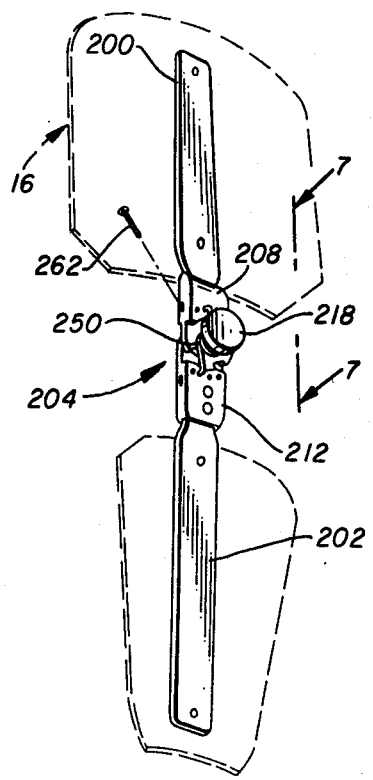
FIG. 6 is a perspective view of a first modification of the knee brace incorporating an alternate hinge.
Figure 7:
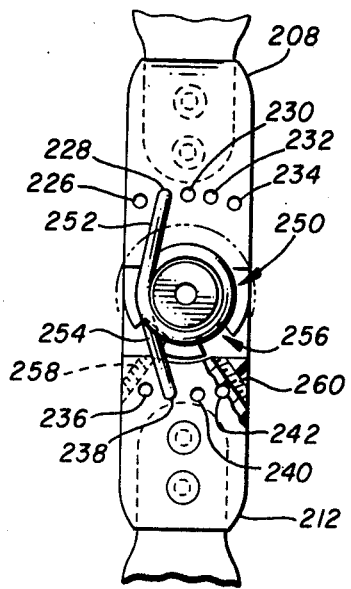
FIG. 7 is a side view of the hinge in the first modification of the knee brace taken along line 7—7 in the direction of the arrows in FIG. 6.
Figure 12:
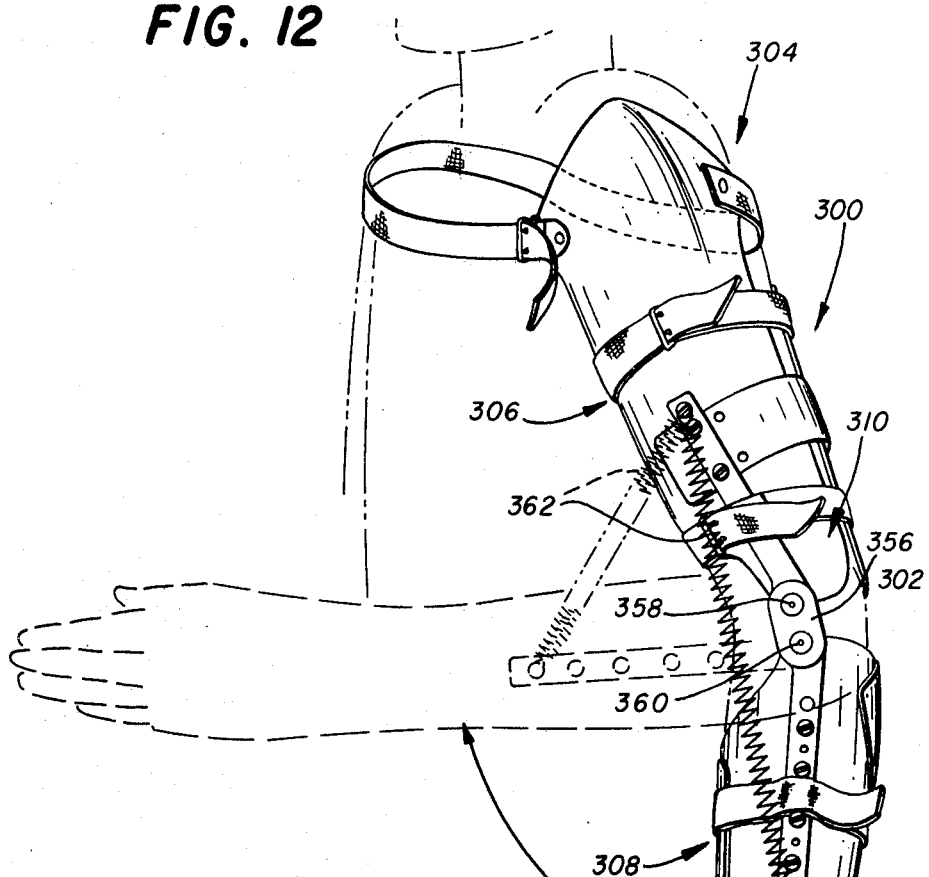
FIG. 12 is a perspective view of a second embodiment of the present invention comprising an elbow brace.

Referring now to the Drawings, wherein like reference characters designate like or corresponding parts throughout several views, FIGS. 1-5 illustrate a first embodiment of the invention forming a knee brace 10.

The knee brace 10 incorporates three major features. The knee brace 10 may be used as a knee immobilizer which permits the knee to be rigidly set to a desired degree of flexion. The knee brace 10 may also be used as a mobilizer. The knee brace will permit the knee joint to be moved within a predetermined arc and the knee brace may also incorporate springs to assist the extension of the knee. Finally, the knee brace 10 may be used in rehabilitation by providing exercise in overcoming resistance from the springs.

The knee brace 10 includes flexible thigh and calf cuffs 12 and 14, and two substantially identical side members 15 and 16. The side members include rigid thigh and calf plates 17 and 18, and thigh and calf stays 20 and 22. The thigh and calf components are connected at hinge members 24 for pivotal motion about an axis X—X corresponding to the axis of pivotal motion of the knee joint 25 when the knee brace 10 is properly positioned on the leg of a patient. A number of thigh straps 26 and calf straps 28 are provided to secure the knee brace 10 to the leg of the patient.

The thigh and calf cuffs 12 and 14 are in direct contact with the patient and are thus made of an appropriate material which allows the skin to breathe so that it will not macerate. The outer portion of the cuffs 12 and 14 are preferably formed of a material having a plurality of loops receptive to engagement with a plurality of small hook-like members extending from an adjacent surface to secure the surface to the cuff. One example of this type of structure is distributed under the tradename Velcro. The cuffs 12 and 14 are wrapped about the thigh and calf of the patient, while leaving a midportion open adjacent the knee joint for dressings, bandages, etc.

Each of the side members 15 and 16 is then placed adjacent the cuffs 12 and 14 so that the pivotal axis of the hinge members 24 correspond to the pivotal axis of the knee joint. The thigh plates 17 and calf plates 18 are formed of a semirigid material, such as plastic, and are shaped generally to conform to the leg of the patient. On the inner surface of thigh plates 17 are mounted two strips 30 having hook-like members for engagement with the outer surface of the thigh cuff 12. Two strips 32 are similarly fastened on the inner surface of the calf plates 18 to engage the outer surface of the calf cuff 14. Both strips 30 and 32 may comprise Velcro fasteners.

The thigh plates 17 and calf plates 18 have a number of holes drilled therethrough to receive bolts 36 for mounting buckles 38 on the outer surface of the plate. Holes are drilled in each of the plates along the medial line thereof to accept bolts 40. The calf stays 22 are secured to the calf plates 18 by bolts 40.

With reference to FIGS. 1-3, the lower portion of the thigh stays 20 include an offset hinge portion 44. The upper end of calf stays 22 include an offset hinge portion 46. A hinge pin 48 passes through apertures 50 and 52 in the hinge portions 44 and 46, respectively to define the pivotal axis X—X between the stays 20 and 22. The head 54 of hinge pin 48 abuts a washer 56 positioned on the inside of hinge portion 46. The end opposite head 54 includes a threaded portion 58 which extends outwardly of the outer surface of hinge portion 44. The hinge pin 48 is secured by a nut 60, pulley 62 and a second washer 56.

Two of the bolts 40 on each side member also fasten brackets 66 to the outer surface of the side member. The lower bracket 66 includes an outwardly turned portion having a hole therein for receiving one end of a spring 68. The upper bracket 66 has a similar outwardly turned portion with a hole to receive one end of a cord 70. The cord is connected adjacent its second end to the free end of spring 68. The midportion of the cord 70 is received in the groove 72 of pulley 62. A plate 74 having matching holes is used to tension the cord 70 as desired.

When positioning side members 15 and 16 on the leg of the patient, the center line of the plates 17 and 18 are positioned on the mid-lateral line on the sides of the leg. The side members may then be secured to the leg by inserting the thigh straps 26 and calf straps 28 through the suitable buckles 38. Each of the straps 26 and 28 may include a strip 80 having a plurality of hook-like members and a strip 82 having a plurality of loops to receive the hook-like members of strip 80. Again, the strips may be formed of Velcro material. While this is the preferred technique for fastening straps 26 and 28, any other suitable fasteners may be employed.

It is readily apparent from the discussion above and the accompanying drawings that the knee brace 10 may be employed on a range of leg sizes while maintaining the center line of each side member in correspondence with the mid-lateral lines of the leg. This overcomes the problem known in the prior art where the stays frequently are anterior or posterior of the mid-lateral line of the leg.

As noted previously, knee brace 10 may be used as an immobilizer for the knee joint. The knee brace 10 further permits the knee joint to be maintained at preselected angles of flexion. This feature is accomplished by the hinge members 24 in a manner described hereinafter.

The hinge portion 46 of calf stays 22 include three threaded apertures 86, 88 and 90 centered on a circle of given radius from the pivot axis and positioned at regular intervals along the circle. The hinge portion 44 of the calf stays 20 includes threaded apertures 92, 94 and 96. The apertures 92, 94 and 96 are also centered along the circle of given radius from the pivot axis and are spaced regularly along the circle.

If the leg of the patient to which knee brace 10 is applied is to be immobilized in the fully extended position, the hinge members 24 must be positioned as shown in FIG. 4. A threaded bolt 98 may be threaded through apertures 94 and 88 to prevent motion in the hinge members 24 from the extended position. The hinge members 24 also permit the knee joint to be immobilized at preselected angles of flexion. In one knee brace constructed under the teachings of the present invention, the apertures 86, 88 and 90 are separated by a 15° arc and the apertures 92, 94 and 96 are separated by a 45° arc. If, for example, a flexion of 60° is desired in the knee joint, the hinge members 24 would be fixed in the position illustrated in FIG. 5. In this position, apertures 86 and 96 will be aligned and a bolt 98 may be threaded through both apertures to immobilize the knee brace 10 at this angle. It is readily apparent that the knee brace 10 may be immobilized at any number of preselected angles limited only by the number of apertures in each hinge portion. The constructed knee brace permits flexion from 0° or full extension, to flexion at 15°, 30°, 45°, and 60° for immobilization.

It will be noted that the apertures are positioned in a symmetrical manner about the center line of the thigh and calf stays so that the side members 15 and 16 may be interchangeable from side to side of the leg of the patient or between the left and right leg of a patient. This reduces the cost of manufacture of knee brace 10.

The knee brace 10 also performs the function of a mobilizer. At the present time, a patient will proceed from a knee immobilizer to therapy to begin range of motion exercises to the knee joint after injury or surgery. The range of motion obtained in the knee joint is usually somewhat difficult at first. It is at times very painful for the individual to flex the knee joint after being immobilized in an extended position for a period of time. Most knee surgery involves incisions on the anterior aspect of the knee joint through the quadriceps expansion. Any tension on this structure will induce pain. This structure is attached to the quadriceps musculature in the anterior aspect of the thigh and any spasticity or spasm of the quadriceps muscle, or involuntary contraction, will put tension on the quadriceps expansion.

The knee brace 10 is designed with springs 68 and cords 70 to provide an extension assist to the patient. When cords 70 are tensioned by the springs, a moment is generated about axis X—X since cords 70 are offset from the axis by pulleys 62. Threaded bolts 98 may be threaded into apertures 92 when the hinge portions are positioned as shown in FIG. 4. The bolts 98 prevent the knee joint from overextending by abutting the surface of notches 100 formed in hinge portions 46. However, the hinge members 24 will permit flexion to any degree.

The tension in springs 68 and cord 70 is adjusted by use of the plate 74 to induce a preselected tension in the fully extended position.

The tensioned cord 70 also provides resistance against which the hamstring muscles in the leg may work. The hamstring muscles are the muscles behind the knee which flex the knee. When the hamstring muscles are actively flexing against a resistance, a reflex inhibition of the neuro function to the quadriceps muscle is present. This allows the maximum relaxation of the quadriceps muscle when the patient is attempting to increase the range of motion in flexion. When the patient relaxes the hamstring muscles, the tensioned cord 70 will cause the knee brace 10 to pivot to the extended position and prevent the patient from using the painful quadriceps muscle during the postoperative state. This feature permits the earlier achievement of a painless range of motion after surgery on the knee joint.

The third feature of the knee brace 10 is its use for rehabilitation of the knee joint and leg of the patient. When the patient has gained adequate range of motion in the knee joint, the patient will typically undergo a series of exercises in an attempt to strengthen the quadriceps muscle. In the past, this exercise has typically been initiated by isometric exercises in which the knee is not taken through any range of motion. The exercise then progresses to straight leg lifting with weights on the ankle of the leg or to a limited arc motion against resistance such as provided by a weight training machine or other weights.

It is often counterproductive for the patient to begin at a full 90° flexion of the knee joint and extend the knee joint against weight. This action places a great deal of stress on the patella femoral joint behind the kneecap. Movement against resistance from approximately a 30° flexion to full extension is less harmful and provides a more beneficial exercise rehabilitation program.

Threaded apertures 108 and 110 are provided on the hinge portions 46 at a given radius from the pivotal axis. Two arcuate slots 112 and 114 are formed in the hinge portions 44 which are also centered about the pivotal axis. By inserting a threaded bolt 98 through apertures 108 and into slots 112, the range of motion of a knee brace 10 will be limited between a predetermined arc, as between 0° and 30° flexion. By pivoting the hinge members 24 to a 30° flexion, a threaded bolt 98 may be threaded through apertures 110 and into slots 114 to limit the pivotal motion to a second predetermined arc, as from 30° to 60° flexion.

If the knee is to be exercised between 0° and 30°, the knee brace 10 may be set accordingly. By moving the cord 70 so as to be received in grooves 72 of pulleys 62 posterior to the knee joint, the tension in cord 70 resist the extension of the leg. The tension cord 70 would urge the knee brace 10 and patient's leg into a 30° flexion. The patient would then be required to exercise the quadriceps muscles to achieve full extension of the knee joint. This would provide a reasonably specific and repeatable resistance through which the patient may do quadriceps exercises. The tension of cord 70 may be adjusted to vary the resistance.

A first modification of the knee brace 10 is illustrated in FIGS. 6-9. Each of the side members 15 and 16 is provided with a thigh stay 200 and calf stay 202 which are somewhat modified from thigh stay 20 and calf stay 22. In addition, the first modification includes hinge members 204 which have some structural differences from hinge members 24 but operate in substantially the same manner. While the hinge members 24, cord 70 and springs 68 are adequate to perform the functions described hereinabove, the first modification of the knee brace 10 forms the preferred construction.

The lower end of each thigh stay 200 includes apertures for accepting threaded screws 206 to secure hinge portion 208 thereto. The upper end of each calf stay 202 has apertures to accept rivets 210 mounting a lower hinge portion 212 thereon.

The upper hinge portion 208 and lower hinge portion 212 are interconnected for pivotal motion about axis Y—Y. When the knee brace 10 is mounted on the leg of a patient, the axis Y—Y will correspond to the pivotal axis of the knee joint. The hinge portions are secured in this relationship by sleeve 214 having a smooth outer surface acting as a bearing and a threaded inner surface, and a bolt 216 threadedly received within the sleeve 214. The bolt 216, in turn, preferably has a threaded central core adapted to receive the threaded end of a thumb screw 218.

The upper hinge portion 208 has apertures 226, 228, 230, 232 and 234 formed therein all lying on a circle of given radius from the pivotal axis Y—Y and equally spaced apart on the circle. The lower hinge portion has similar apertures 236, 238, 240, 242 formed therein lying on the identical circle and equally spaced. The apertures 226–234 are adapted to receive the first leg 252 of a torsion spring 250. The second leg 253 of the torsion spring is received in one of the apertures 236–242. The torsion spring 250 is retained with its legs in engagement with apertures and centered about the pivotal axis by contact with the thumb screw 218.

The upper hinge portion 208 also includes two slots 254 and 256 at the outer end thereof. These slots are positioned in alignment with oblique threaded holes 258 and 260 in the lower hinge portion 212 within a predetermined range of flexion. The threaded holes 258 and 260 are adapted to receive a threaded screw 262 as shown in FIG. 9. As can readily be seen, the hinge member 204 is reversible and may be used on either side of the knee, or either leg.

The lower hinge portion 212 includes slots 255 and 257 at the outer end thereof. These slots are aligned with oblique threaded holes 259 and 261 in upper hinge portion 208 within a predetermined range of flexion. The threaded holes 259 and 261 are adapted to receive a screw 262.

The first modification of knee brace 10 performs substantially all the functions described hereinabove. The bolt 216 is constructed of a material, such as plastic, with some resiliency so that the thumb screws 218 on both side members of the knee brace may be tightened to deform the bolts and prevent pivotal motion between the two hinge portions. The knee joint of the patient may then be immobilized at a desired degree of deflection by merely tightening the thumb screw 218. When knee brace 10 is employed as an immobilizer, the torsion springs 250 need not be in place in the apertures.

The slots 254 and 256 are preferably sized and positioned so that a bolt threaded through bolt hole 258 or 260 will be received within slot 254 or 256 when the angle of flexion of the knee is between 0° and 30°. The slots 255 and 257 are sized and positioned so that a bolt 262 extending through threaded hole 259 or 261 will enter the slot when the angle of flexion of the knee joint is between 30° and 60°. Therefore, a limited range of motion is provided, at whatever arc desired, by properly sizing slots 254–257.

By positioning the torsion spring 250 within the apertures so that the spring creates a movement about the pivotal axis and urges the knee joint to full extension, a knee mobilizer is provided which relieves the necessity to exert the quadriceps muscles. The degree of spring tension may be adjusted by moving the legs 252 and 253 to different apertures.

The torsion spring 250 may also be used to resist motion in either direction in the arc determined by slots 254–257. The resistance in one direction is readily transformed to resistance in the opposite direction by removing the thumb screw 218 and reversing the positioning of the torsion spring 250 on the hinge portions.

While the use of a torsion spring such as 250 is the preferred construction, the tension cord 70 or any other provisions for creating a movement about the pivotal axis would be suitable for use in the knee brace 10. For example, memory rods may be used provide the movement. Rubber bands may also be interconnected between the hinge portions in either side member 15 or 16 to provide the movement.

In a second modification of the knee brace 10 illustrated in FIGS. 10 and 11, the threaded holes 257–261, sleeve 214 and bolt 216 are eliminated. A threaded bolt 268 and pin 270 are mounted on a backing plate 272 with centers at a distance R apart. The threaded bolt 268 passes through the hinge portions to provide pivotal motion about the axis Y—Y. The pin 270 extends either through an aperture 274 or adjacent surfaces 275 or 277 formed the lower hinge portion 212. The pin extends from the opposite side of the lower hinge portion and may be received in one of apertures 276, 278, 280 and 282. A series of slots 283 and 284 are also provided in the upper hinge portion. To limit the arc from full extension to a desired flexion, a pin 286 is passed through either aperture 278 or 280 to abut against surfaces 288 or 290 to prevent over-extension. The pin 270 is then positioned in the aperture providing the desired flexion. For example, pin 270 may pass through aperture 282 to provide 0° to 30° flexion. The knee joint may be immobilized at varied degrees of flexion by positioning pin 270 and one or more pins 286. Slots 283 or 284 are formed within the upper hinge portion to limit arc motion in cooperation with pin 270, from 30° to 60° flexion for example. Each of the apertures and slots are centered at a distance R from the pivotal axis of the hinge member. The apertures and slots are again adapted so that the pin 270 will permit the knee brace 10 to be immobilized at predetermined degrees of deflection and also limited in pivotal motion in a given arc. A modified thumb screw 218 is threaded onto the end of bolt 264 to maintain the bolt and pin in engagement with the hinge portions and may be used to tighten bolt 268 to immobolize the knee.

A second embodiment of the present invention is illustrated in FIGS. 12–15 and forms an elbow brace 300. The elbow brace 300 is adapted for supporting the elbow 302 and adjoining tissue on a patient's arm 304. The elbow brace generally includes three major sections. The upper arm section 306 is interconnected to the lower arm section 308 by a hinge member 310.

The upper arm section 306 includes an outer plate 312 shaped to fit over the outside of the upper arm and shoulder. An inner plate 314 is shaped to fit the inner part of the upper arm adjacent the chest. An interconnecting member 316 is riveted to both plates 312 and 314 by rivets 318. In the preferred construction, the plates 312 and 314 and member 316 are formed of semirigid material, such as plastic. Straps 320 including buckles 322 at one end are provided to strap the plates 312 and 314 about the upper arm portion. A shoulder strap 324 is provided to wrap about the shoulders of the patient and to a buckle 322 thereon to further support the plates on the patient as shown in FIG. 1.

The lower arm section 308 includes a back plate 330 and a front plate 332 which cooperate to substantially encase the lower arm of the patient. In the preferred embodiment, one of the plates, such as back plate 330, has strips 334 secured thereon including loops for interlocking with flexible hooks on straps 336 attached to the other plate. Again, the strips 334 and straps 336 may comprise the fastener known as Velcro. However, any suitable means for securing the plates 312 and 314 and 330 and 332 would be adequate.

An upper arm stay 340 is secured to both outer plate 312 and member 316 by a number of threaded bolts 342. A lower arm stay 344 is secured to the back plate 330 by bolts 342.

Figure 14:
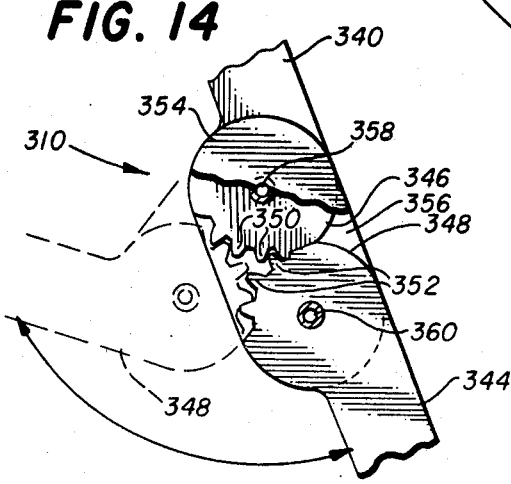
FIG. 14 is a side view of the hinge used in the elbow brace.
Figure 13:
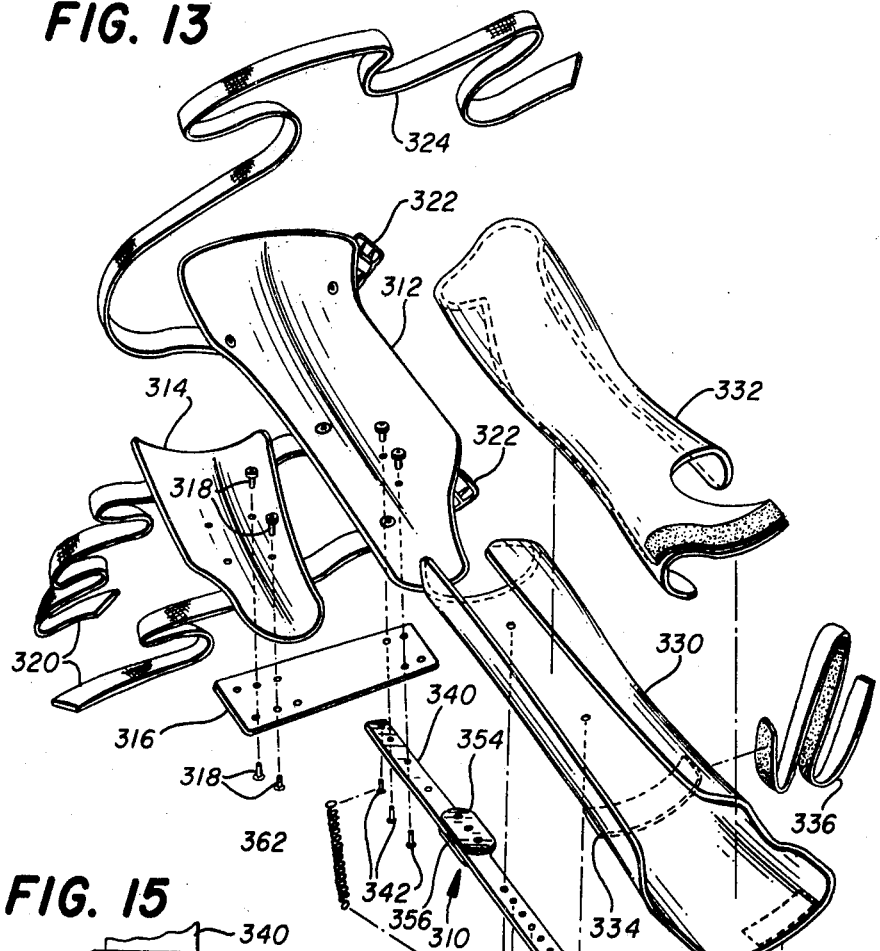
FIG. 13 is an exploded view of the elbow brace.

The hinge member 310 interconnects the stays 340 and 344 for pivotal motion about an axis corresponding substantially to the pivotal axis of the elbow and forms a polycentric hinge. The stays 340 and 344 each end in portion 346 and 348 having interlocking gear teeth 350 and 352 as best shown in FIG. 14. Plates 354 and 356 are secured on either side of the end portions of the stays and are pivotally mounted thereto by pins 358 and 360. The pivotal motion of the hinge member 310 is illustrated in FIG. 14. The full line corresponds to the position of the hinge member when the arm is fully extended and the dotted line represents the position of stay 344 when the elbow has been flexed.

A coiled spring 362 is interconnected between bolts 342 on the upper and lower arm stays 340 and 344. The spring urges the elbow brace 300 and arm 304 into the bent position illustrated in phantom line in FIG. 12. This position represents the most suitable position for recovery from injury or surgery. The spring also acts to exercise the tricep muscles at the posterior of the upper arm while inhibiting contraction of the bicep muscles.

Figure 15:
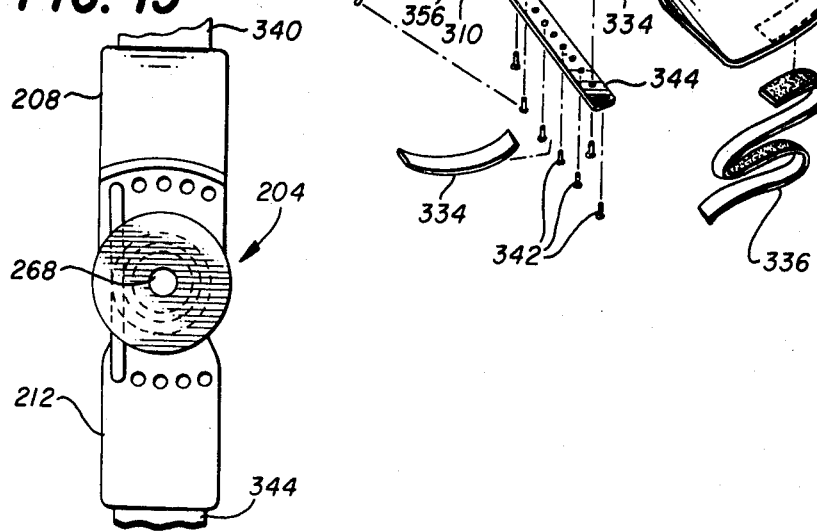
FIG. 15 is a side view of a hinge used in a first modification of the elbow brace.

In the first modification of elbow brace 300, illustrated in FIG. 15, a hinge member 204 replaces the hinge member 310 and spring 362. The hinge member 204 permits reduction in the size of the hinge member.

Referring now to FIGS. 16, 17, and 18, there is shown a knee brace 400 comprising a third embodiment of the invention. The knee brace 400 includes a thigh plate 402 formed from a relatively flexible material, such as one of the various thermoplastic materials. The thigh plate 402 is secured to a thigh stay 404 by means of suitable fasteners 406, such as rivets. The thigh stay 404 is formed from a relatively rigid material, for example, a metal such as aluminum. The thigh stay 404 in turn extends to a first hinge portion 408 which is secured to the thigh stay 404 by means of suitable fasteners 410, such as rivets.

The knee brace 400 further includes a calf plate 412 formed from a relatively flexible material such as one of the various thermoplastic materials. The calf plate 412 is secured to a calf stay 414 by means of a plurality of fasteners 416, such as rivets. The calf stay 414 is formed from a relatively rigid material, for example, one of the various metals such as aluminum. The calf stay 414 is secured to a second hinge portion 418 by means of a plurality of fasteners 420, such as rivets.

Referring to FIG. 17, the first hinge portion 408 of the knee brace 400 is formed from a suitable plastic material such as nylon. A pin receiving aperture 422 is formed in the first hinge portion adjacent the fasteners 410. A bolt receiving aperture 424 extends through the first hinge portion. The first hinge portion 408 has an inwardly directed face 426 which surrounds the bolt receiving aperture 424. The face 426 is characterized by a plurality of relatively small teeth 428 which are circumferentially equally spaced about the axis of the bolt receiving aperture 424.

The second hinge portion 418 is also formed from a suitable plastic material such as nylon. The second hinge portion 418 has three pin receiving apertures 432 formed therein. A bolt receiving aperture 434 extends through the second hinge portion 418. The second hinge portion 418 has an inwardly directed face 436 comprising a plurality of tooth receiving slots 438a, 438b, 438c and 438d. The tooth receiving slots 438a, 438b, 438c an 438d are similar in shape, but each of the tooth receiving slots has a different circumferential dimension with the slot 438a being the smallest, the slot 438b being larger than the slot 438a, but smaller than the slot 438c, the slot 438c being larger than the slot 438b, but smaller than the slot 438d, and the slot 438d being the largest.

An adjusting disc 440 is positioned between the first hinge portion 408 and the second hinge portion 418. The adjusting disc 440 has a first circular face 442 positioned in facing relationship to the face 426 of the first hinge portion 408 and a second circular face 444 positioned in facing relationship to the face 436 of the second hinge portion 418. A bolt receiving aperture 446 extends through the adjusting disc 440 in alignment with the bolt receiving aperture 424 of the first hinge portion 408 and the bolt receiving aperture 434 of the second hinge portion 418.

The first circular face of the adjusting disc 440 comprises a plurality of relatively small, circumferentially equally spaced teeth 448. The teeth 448 of the first circular face 442 of the adjusting disc 440 are adapted for meshing engagement with the teeth 428 of the face 426 of the first hinge portion 408. With the teeth 448 and 428 so engaged, the adjusting disc 440 and the first hinge portion 408 are locked against pivotal movement relative to each other. It will be understood that since the teeth 448 and 428 are equally spaced around the axis of the apertures 424 and 446, the teeth 448 may be meshed with the teeth 428 to prevent relative pivotal movement between the disc 440 and the first hinge portion 408 regardless of the rotational positioning of the disc 440.

The second circular face 444 of the adjusting disc 440 comprises a single, relatively large tooth 450. The tooth 450 of the second circular face 444 of the adjusting disc 440 is adapted for positioning in a selected slot 438a, 438b, 438c or 438d to control relative pivotal movement between the second hinge portion 418 and the adjusting disc 440, and therefore the first hinge portion 408.

The tooth 450 is substantially identical in shape and in circumferential dimension to the slot 438a of the face 436 of the second hinge portion 418. Therefore, when the tooth 450 is engaged with the slot 438a relative pivotal movement between the second hinge portion 418 and the adjusting disc 440 is prevented. Since the engagement of the teeth 448 of the adjusting disc 440 with the teeth 428 of the first hinge portion 408 prevents relative pivotal movement between the adjusting disc 440 and the first hinge portion 408, the positioning of the tooth 450 in the slot 438a effectively prevents relative pivotal movement between the first hinge portion 408 and the second hinge portion 418. The slot 438b is somewhat larger in circumferential dimension than the slot 438a. Therefore, if the tooth 450 of the adjusting disc 440 is positioned in the slot 438b of the second hinge portion 418, a limited amount of pivotal motion of the second hinge portion 418 relative to the adjusting disc 440 is permitted. This in turn permits limited pivotal movement of the first hinge portion 408 relative to the second hinge portion 418. Likewise, since the slot 438c is somewhat larger in circumferential dimension than the slot 438b, and since the slot 438d is in turn somewhat larger in circumferential dimension than the slot 438c, the positioning of the tooth 450 in the slot 438c ultimately permits more pivotal movement of the first hinge portion 408 relative to the second hinge portion 418 than is permitted when the tooth 450 is engaged with the slot 438b, and the positioning of the tooth 450 in the slot 438d permits even more pivotal movement of the first hinge portion 408 relative to the second hinge portion 418 than is permitted when the tooth 450 is engaged with the slot 438c.

A brass bushing 452 is positioned in the bolt receiving aperture 434 of the second hinge portion 418. A bolt 454 is received through the bushing 452, the bolt receiving aperture 446 of the adjusting disc 440 and the bolt receiving aperture 424 of the first hinge portion 408 so that the second hinge portion 418 is supported for pivotal movement relative to the bolt 454. A metal washer 456 and a nylon washer 458 are utilized to reduce frictional drag. A knob 460 is threadedly engaged with the bolt 454 and functions to retain the teeth 428 of the first hinge portion 408 in mesh with the teeth 448 of the adjusting disc 440 and to retain the tooth 450 of the adjusting disc 440 in engagement with a selected slot 438a, 438b, 438c or 438d of the second hinge portion 418.

Referring now to FIG. 18, the knee brace 400 may be utilized either with or without a torsion spring 462. When the torsion spring 462 is used, the bolt 454 of FIG. 17 is replaced by a longer bolt 464. Otherwise, the knee brace 400 comprises exactly the same components regardless of whether or not the torsion spring 462 is used.

The bolt 464 extends through a plastic bushing 466 which in turn supports the torsion spring 462 in axial alignment with the first hinge portion 408, the adjusting disc 440 and the second hinge portion 418. The torsion spring 462 has projections 468 and 470 extending axially from the opposite ends thereof. The projection 468 is received in the aperture 422 formed in the first hinge portion 408. By this means, one end of the torsion spring 462 is secured to the first hinge portion 408 for pivotal movement therewith.

The projection 470 of the torsion spring 462 is positioned in a selected aperture 432 formed in the second hinge portion 418. By this means the second end of the torsion spring 462 is secured to the second hinge portion 418 for pivotal movement therewith.

The positioning of the projection 470 in a selected aperture 432 may be utilized to preload the knee brace 400 for pivotal movement in a selected direction. Thus, if the component parts of the knee brace 400 are assembled to position the thigh stay 404 and the calf stay 414 is shown in FIG. 16, and if the projection 470 is positioned in the centermost aperture 432, the component parts of the knee brace 400 are not preloaded toward pivotal movement in either direction. If the projection 470 is positioned in the right hand (FIG. 18) aperture 432, the component parts of the knee brace 400 are preloaded to pivot in the counterclockwise direction (FIG. 18). Conversely, if the projection 470 is positioned in the left hand (FIG. 8) aperture 432, the component parts of the knee brace 400 are preloaded to pivot in the counterclockwise direction (FIG. 18).

The knee brace 400 is utilized similarly to the utilization of the knee brace 10 as shown in FIG. 1. A thigh cuff is positioned around the thigh of the patient, and a calf cuff is positioned around the calf of the patient. The knee brace 400 is then positioned on the leg of the patient with the thigh plate 402 engaging the thigh cuff and the calf plate 412 engaging the calf cuff. Preferably, two knee braces 400 are used, one on each side of the leg. The knee braces are positioned with the thigh stays 404 and the calf stays 414 thereof aligned with the midlateral line of the leg.

The knee braces 400 are then secured in place. Although any conventional securing mechanism may be used, the knee braces 400 are preferably secured in place on the leg of the patient by means of straps of the type illustrated in FIG. 1. The use of straps to secure the knee braces 400 in place is facilitated by providing the thigh plates 402 and the calf plates 412 of the knee braces with conventional strap fittings which may be secured in place by rivets. The straps may be formed from various conventional strapping materials, for example, nylon webbing. The straps may be provided with conventional buckles, or the straps may be provided with closures of the type sold under the trademark "VELCRO".

The use of the knee braces 400 also involves the selection of the appropriate slot 438a, 438b, 438c or 438d of the second hinge portion 418 to receive the tooth 450 of the adjusting disc 440. If the tooth 450 is positioned in the slot 438a, the second hinge portion 418 is locked against pivotal movement relative to the adjusting disc 440. If the tooth 450 is positioned in the slot 438b, the second hinge portion 418 is allowed to pivot relative to the adjusting disc 440 through an arc of approximately 30°. If the tooth 450 is positioned in the slot 438c, the second hinge portion 418 is allowed to pivot relative to the adjusting disc 440 through an arc of approximately 50°. If the tooth 450 is positioned in the slot 438d, the second hinge portion 418 is allowed to pivot relative to the adjusting disc 440 through an arc of approximately 70°. Of course, the particular sizes of the slots 438a, 438b, 438c and 438d relative to the size of the tooth 450 may be selected in order to fulfill the requirements of particular applications of the invention.

The use of the knee braces 400 further includes the selection of the appropriate angular relationship of the thigh plate 402 and the thigh stay 404 relative to the calf plate 412 and the calf stay 414 in accordance with the therapeutic needs of a particular patient. This is accomplished by simply bringing the component parts of the knee braces 400 into the required angular relationship and then securing the parts in the required angular relationship by engagement of the teeth 428 of the face 426 of the first hinge portion 408 with the teeth 448 of the face 442 of the adjusting disc 440. It will thus be understood that the positioning of the tooth 450 of the adjusting disc 440 in a particular slot 438a, 438b, 438c or 438d of the second hinge portion 418 regulates the amount of angular movement that is permitted between the thigh plate 402 and the calf plate 412, and that regardless of the amount of angular motion that is permitted, the required angular relationship between the thigh plate 402 and the calf plate 412 may be established utilizing the teeth 428 of the first hinge portion 408 and the teeth 448 of the adjusting disc 440. In this manner the therapy of the knee is facilitated by permitting the knee to pivot through any selected arc, and by establishing the beginning and ending points of the arc at any desired angular relationship.

Yet another aspect of the use of the knee braces 400 involves the torsion springs 462. It will be understood that in some instances the torsion springs 462 are not utilized at all. However, when it is desired to preload the knee braces 400 with a predetermined torque, the torsion springs 462 are utilized in the manner shown in FIG. 18. The selection of a particular aperture 432 of the second hinge portion 418 to receive the projection 470 of the torsion spring 462 determines the degree of preloading that is imposed on the component parts of the knee braces 400 by the torsion springs 462.

Although particular embodiments of the invention have been illustrated in the accompanying drawings and described in the foregoing detailed description, it will be understood that the invention is not limited to the embodiments disclosed, but is capable of numerous rearrangements, modifications, and substitutions of parts and elements without departing from the spirit of the invention.

What is claimed is:

1. A hinge joint for a knee brace comprising:
    an adjusting disc having opposed first and second circular faces;
    the first circular face of the adjusting disc comprising a plurality of first teeth positioned at circumferentially equally spaced points;
    the second circular face of the adjusting disc comprising a tooth having a predetermined circumferential dimension;
    a first hinge portion comprising a face having a plurality of teeth positioned at circumferentially equally spaced points and dimensioned to mate with the teeth of the first circular face of the adjusting disc to lock the adjusting disc and the first hinge portion against rotational movement with respect to each other;
    a second hinge portion comprising a face having a plurality of slots formed therein, each for selective mating engagement with the tooth of the second circular face of the adjusting disc and each characterized by a different circumferential dimension so that the tooth of the second circular face of the adjust disc and the slots of the face of the second hinge portion permit relative pivotal movement between the second hinge portion and the adjusting disc, depending upon which of the slots receives the tooth; and
    fastening means extending through the first and second hinge portions and the adjusting disc for maintaining the teeth of the first circular face of the adjusting disc in mating engagement with the teeth of the face of the first hinge portion and for maintaining the tooth of the second circular face of the adjusting disc in engagement with a selected slot of the face of the second hinge portion.

2. The hinge joint for a knee brace according to claim 1 wherein one of the slots of the face of the second hinge portion has a circumferential dimension substantially identical to the circumferential dimension of the tooth of the second circular face of the adjusting disc so that engagement of the tooth with said one of the slots locks the second hinge portion against pivotal movement relative to the adjusting disc.

3. The hinge joint for a knee brace according to claim 1 wherein the face of the second hinge portion comprises at least three slots;
    the first of said slots having a circumferential dimension substantially identical to that of the tooth of the second circular face of the adjusting disc so that engagement of the tooth with said first of the slots locks the second hinge portion against pivotal movement relative to the adjusting disc;
    a second of said slots having a circumferential dimension substantially greater than that of the tooth of the second circular face of the adjusting disc so that engagement of the tooth with said second slot permits substantial pivotal movement of the second hinge portion relative to the adjusting disc; and
    a third of said slots having a circumferential dimension substantially greater than that of said second slot so that engagement of the tooth of the second circular face of the adjusting disc with said third slot permits substantially lower pivotal movement of the second hinge portion relative to the adjusting disc than is permitted when the tooth is engaged with said second slot.

4. The hinge joint for a knee brace according to claim 3 wherein the fastening means comprises a bolt extending through the second hinge portion, the adjusting disc and the first hinge portion and a knob threadedly engaged with the bolt for maintaining engagement between the face of the first hinge portion and the first circular face of the adjusting disc and between the face of the second portion and the second circular face of the adjusting disc, and further including a bushing mounted in the second hinge portion and engaging the bolt to facilitate pivotal movement of the second hinge portion relative to the bolt.

5. The hinge joint for a knee brace according to claim 4 further characterized by:
    a spring receiving aperture formed in the first hinge portion;
    at least one spring receiving aperture formed in the second hinge portion;
    a spring supporting bushing mounted on the bolt;
    a torsion spring mounted on the spring supporting bushing and having projections extending axially from the opposite ends thereof;
    one of the projections of the torsion spring engaging the spring receiving aperture of the first hinge portion and the other projection of the torsion spring engaging the spring receiving aperture of the second hinge portion.

6. The hinge joint for a knee brace according to claim 5 wherein at least one of the hinge portions has a plurality of spring receiving apertures formed therein so that the torque that is applied to the hinge joint by the torsion spring depends on the positioning of one of the projections of the torsion spring in a selected spring receiving aperture of one of the hinge portions.

7. A knee brace comprising:
    a thigh plate shaped to conform to the thigh of the leg;
    a calf plate shaped to conform to the calf of the leg;
    said thigh plate and calf plate being positioned on the thigh and calf when the knee brace is mounted on the leg so that the center line of said thigh and calf plates lies on the mid lateral line of the leg;

a thigh stay secured to the thigh plate and extending to a first hinge portion adjacent the knee joint when positioned on the leg;

a calf stay secured to the calf plate and extending to a second hinge portion adjacent the knee joint when positioned on the leg;

said first hinge portion comprising a face including a plurality of circumferentially equally spaced teeth;

said second hinge portion comprising a face having a plurality of slots formed therein, each of said slots being characterized by a circumferential dimension which is substantially different from the circumferential dimension of the remaining slots;

an adjusting disc positioned between the first and second hinge portions and comprising first and second circular faces;

a first circular face of the adjusting disc having a plurality of circumferentially equally spaced teeth dimensioned and positioned for meshing engagement with the teeth of the face of the first hinge portion to lock the adjusting disc against pivotal movement relative to the first hinge portion;

the second circular face of the adjusting disc having a tooth formed thereon characterized by a predetermined circumferential dimension so that the engagement of the tooth of the second circular face of the adjusting disc with a predetermined slot of the second hinge portion regulates the pivotal movement of the second hinge portion relative to the adjusting disc; and fastening means for maintaining the face of the first hinge portion in engagement with the first circular face of the adjusting disc and for maintaining the face of the second hinge portion in engagement with the second circular face of the adjusting disc.

8. The knee brace according to claim 7 wherein the slots of the face of the second hinge portion are further characterized by:

a first slot having a circumferential dimension which is substantially identical to that of the tooth of the second circular face of the adjusting disc so that engagement of the tooth with the first slot prevents pivotal movement of the second hinge portion relative to the adjusting disc;

a second slot having a circumferential dimension which is substantially greater than that of the tooth of the second circular face of the adjusting disc so that engagement of the tooth with the second slot permits a predetermined amount of pivotal movement of the second hinge portion relative to the adjusting disc; and a third slot having a circumferential dimension which is substantially greater than that of the second slot so that engagement of the tooth of the second circular face of the adjusting disc with the third slot permits substantially greater pivotal movement of the second hinge portion relative to the adjusting disc than is permitted when the tooth is engaged with the second slot.

9. The knee brace according to claim 8 wherein each of the first and second hinge portions has at least one spring receiving aperture formed therein, and further including a torsion spring having projections extending axially from the opposite ends thereof, said projections of the torsion spring being received in the spring receiving apertures of the first and second hinge portions so that the torsion spring applies a predetermined torque to the knee brace, and wherein the fastening means also retains the projections of the torsion spring in engagement with the spring receiving apertures of the first and second hinge portions.

10. The knee brace according to claim 9 wherein the fastening means comprises:

a bolt extending through the first and second hinge portions and the adjusting disc;

a bushing mounted in the second hinge portion and engaging the bolt for pivotally supporting the second hinge portion thereon, a spring supporting bushing mounted on the bolt;

said torsion spring being supported on the spring supporting bushing;

a knob threadedly engaging the bolt for retaining the face of the first hinge portion in engagement with the first circular face of the adjusting disc, for retaining the face of the second hinge portion in engagement with the second circular face of the adjusting disc, and for retaining the projections of the torsion spring in engagement with the spring receiving apertures of the first and second hinge portions.

* * * * *